US010775400B2

(12) United States Patent
Eberle

(10) Patent No.: US 10,775,400 B2
(45) Date of Patent: Sep. 15, 2020

(54) FEEDING APPARATUS

(71) Applicant: ANDREAS HETTICH GMBH & CO. KG, Tuttlingen (DE)

(72) Inventor: Klaus-Guenter Eberle, Tuttlingen (DE)

(73) Assignee: ANDREAS HETTICH GMBH & CO. KG, Tuttlingen (DE)

( * ) Notice: Subject to any disclaimer, the term of this patent is extended or adjusted under 35 U.S.C. 154(b) by 543 days.

(21) Appl. No.: 15/442,377

(22) Filed: Feb. 24, 2017

(65) Prior Publication Data

US 2017/0254826 A1    Sep. 7, 2017

(30) Foreign Application Priority Data

Mar. 1, 2016  (DE) .................. 10 2016 103 639

(51) Int. Cl.
  *G01N 35/04*  (2006.01)
  *C12M 3/00*  (2006.01)
  (Continued)

(52) U.S. Cl.
  CPC ............. *G01N 35/04* (2013.01); *C12M 23/10* (2013.01); *C12M 23/48* (2013.01); *C12Q 1/02* (2013.01);
  (Continued)

(58) Field of Classification Search
  CPC ............. G01N 35/04; G01N 35/00623; G01N 35/00732; G01N 35/00871;
  (Continued)

(56) References Cited

U.S. PATENT DOCUMENTS 617,478 A  *  1/1899  Cohen .................... A47F 5/01
                                                            211/49.1

4,170,861 A  *  10/1979  Snyder ................. B65B 7/2807
                                                            53/109
(Continued)

FOREIGN PATENT DOCUMENTS

CN        101970637      2/2011
DE       102010044125    5/2012
(Continued)

OTHER PUBLICATIONS

German Patent and Trademark Office, Search Report, dated Oct. 28, 2016, pp. 1-10, Application No. 102016103639.0, Applicant: Andreas Hettich Gmbh & Co. KG.
(Continued)

*Primary Examiner* — William H. Beisner
*Assistant Examiner* — Danielle B Henkel
(74) *Attorney, Agent, or Firm* — Woodling, Krost and Rust

(57) ABSTRACT

The invention relates to a feeding system (10) having a feeding apparatus (30) for conveying laboratory vessels for samples, microorganisms, cell cultures or the like, and a carrier (12) having one or plural holders (16) for storing laboratory vessels, which feeding apparatus (30) has a loading area (36) and an unloading area (46) remote from the loading area (36) in which plural laboratory vessels can be stored in a vertically stacked configuration, with each receiving unit (34) being coupled to an endless conveyor unit (38) which transports the receiving unit (34) from the loading area (36) to the unloading area (46), and in which the carrier (12) can be used to introduce laboratory vessels into one or plural receiving units (34) in the loading area (36), for which purpose the carrier (12) is at least partially slid over the at least one receiving unit (34) which is to be loaded or unloaded, and for this purpose has projections (28, 32) and/or recesses that are associated with the carrier (12) and are provided in the loading area (36) of the feeding apparatus (30), which will result in positive locking of the feeding apparatus (30) and the carrier (12) when the carrier (12) has been inserted in the loading area (36). According to the
(Continued)

invention, the carrier (12) has at least two holders (16) and the positive locking of the carrier (12) and the receiving unit (34) in the loading area (36) of the feeding apparatus (30) will allow only a single predefined orientation of the carrier (12) in the loading area (36).

15 Claims, 5 Drawing Sheets

(51) Int. Cl.
    *C12M 1/22*     (2006.01)
    *C12Q 1/02*     (2006.01)
    *G01N 35/00*     (2006.01)

(52) U.S. Cl.
    CPC . *G01N 35/00623* (2013.01); *G01N 35/00732* (2013.01); *G01N 35/00871* (2013.01); *G01N 2035/00643* (2013.01); *G01N 2035/0427* (2013.01); *G01N 2035/0465* (2013.01)

(58) Field of Classification Search
    CPC . G01N 2035/00643; G01N 2035/0427; G01N 2035/0465; C12M 23/10; C12M 23/48; C12Q 1/02
    See application file for complete search history.

(56) References Cited

U.S. PATENT DOCUMENTS

| | | | | |
|---|---|---|---|---|
| 4,468,914 A * | 9/1984 | Pestes | ............ | C12M 23/10 141/102 |
| 5,020,297 A * | 6/1991 | Borie | ............ | B65B 43/44 141/130 |
| 5,698,260 A * | 12/1997 | Roth | ............ | B05C 7/04 118/306 |
| 8,561,376 B2 * | 10/2013 | Brelivet | ............ | C12M 99/00 141/130 |
| 8,691,558 B2 * | 4/2014 | Gupta | ............ | C12M 33/02 435/286.3 |
| 2010/0173416 A1 | 7/2010 | Gupta et al. | | |
| 2011/0027863 A1 | 2/2011 | Beese | | |
| 2012/0251275 A1 * | 10/2012 | Malin | ............ | G01N 35/0099 414/225.01 |
| 2015/0276566 A1 * | 10/2015 | Berntsen | ............ | G01N 35/021 435/309.1 |

FOREIGN PATENT DOCUMENTS

| | | |
|---|---|---|
| DE | 102015207617 | 10/2016 |
| EP | 1018544 | 7/2000 |
| EP | 2482079 | 8/2012 |

OTHER PUBLICATIONS

European Patent Office, European Extended Search Report, dated Aug. 21, 2017, pp. 1-6, Application No. 16206829.0, Applicant: Andreas Hettich Gmbh & Co. KG.

IUL Instruments, Plate Handler, Feb. 28, 2016, pp. 1-2, URL:http://www.iul-inst.com/images/6094R01.pdf.

China National Intellectual Property Administration, First Office Action Notification, Office Action, dated Aug. 29, 2019, pp. 1-8.

China National Intellectual Property Administration, English Translation of First Office Action Notification, Office Action, dated Aug. 29, 2019, pp. 1-7.

* cited by examiner

FEEDING APPARATUS

This patent application claims the benefit and priority of and to German patent application no. 10 2016 103 639.0, filed Mar. 1, 2016. This patent application incorporates German patent application no. 10 2016 103 639.0, filed Mar. 1, 2016, by reference hereto in its entirety.

The invention relates to an apparatus for feeding laboratory vessels.

Various approaches are already known in the prior art for feeding laboratory vessels, usually Petri dishes, to systems for processing and analyzing microorganisms and cell cultures, which thus reduce the manual workload of a user to a minimum. It is common practice to introduce stacks of Petri dishes into a loading area from where they are then individually conveyed to the next step, for example to an analysis or a preparation unit. Furthermore, it is tried to introduce several stacks at a time into the system so as to increase the periods between the loading steps and thus give the user time to do other work.

IUL, S.A., for example, proposes a sample changer (plate handler) having an integrated handler which is loaded with a Petri dish carrier filled with Petri dishes. The carrier has four holders for vertical stacks of Petri dishes and—once loaded into the apparatus—can be rotated about its own axis, in the manner of a carrousel. A conventional drive motor is provided for the rotary movement of the carrier. In an unloading zone, a stack of Petri dishes is removed from a holder and moved horizontally towards the analysis unit. In this position, an elevator is provided which is used to feed the Petri dishes individually to the analysis unit and to remove them again from the analysis unit once analysis has been completed. After analysis of all the Petri dishes contained in the stack, the stack is carried back to the carrier and inserted in the original holder again. Then a conveyor unit rotates the carrier until the next full holder can be accessed for the removal of Petri dishes.

This solution allows the carrier to be loaded with up to four stacks of Petri dishes and to feed these Petri dishes to the analysis unit without any user intervention. However, the holder remains in the carrier and cannot be used for loading and conveying further Petri dishes for the entire analysis process. Moreover, every time an entire stack of Petri dishes is removed from a holder and subsequently put back again, there is the danger of the stack becoming instable and the Petri dishes shifting in the stacks or even falling down. Furthermore, the unloading zone is not easily accessible, and removal of the carrier may be required prior to repairing defects.

German patent application DE 10 2015 207 617.2, which has not yet been published, discloses a carrier for receiving and storing laboratory vessels which already presents an approach for solving the above mentioned problems.

The carrier has a plurality of holders for receiving and storing laboratory vessels. Each holder has a loading opening at the top of the carrier and an unloading opening at the bottom of the carrier which can be closed by a closing mechanism. The unloading opening is closed when the carrier is being loaded with laboratory vessels, and during transport. Once the carrier has been inserted into a magazine of a feeding apparatus for laboratory vessels, the closing mechanism is opened and the carrier is removed from the magazine, with the laboratory vessels remaining in the magazine. In this way, the stacks of laboratory vessels contained in the holders of the carrier will be safely transferred to the magazine. During analysis, however, the carrier will be available for storing and transporting other laboratory vessels. Moreover, the laboratory vessels can be accessed more easily in the magazine without the carrier in place, which will facilitate repair work.

However, it has sometimes proved difficult in practice to clearly identify the position of specific laboratory vessels at any time once these have been introduced into the magazine. Especially when sensors for detecting the position of laboratory vessels are defect, it may be unclear in the case of a mechanical failure which laboratory vessels have already been processed in the absence of the operator.

It is the object of the invention to further develop a feeding system that does not exhibit the above mentioned shortcomings and allows the exact position of laboratory vessels within the feeding apparatus to be identified at any time, even in the case of malfunctions.

The invention is based on the finding that the positions of laboratory vessels, in particular stacks of laboratory vessels, within the feeding apparatus, can be identified more easily when a clearly defined scheme is specified for loading the feeding apparatus by the carrier.

In the embodiment according to the invention, the carrier has at least two holders, and the positive locking of the carrier and the receiving unit in the feeding apparatus loading area only allows one specific orientation of the carrier in the loading area. Consequently, when the laboratory vessels are fed from the carrier to the loading area, one or more stacks of laboratory vessels can clearly be allocated to one receiving unit. This facilitates the simultaneous handling of laboratory vessels with different contents and reduces the likelihood of a mix-up. A mix-up of samples may have disastrous consequences, e.g. incorrect diagnoses of patient samples etc. A reduced likelihood of a mix-up increases patient safety and diminishes the risk of incorrect diagnoses. Moreover, this also saves a considerable amount of time.

In yet another advantageous embodiment, the receiving unit may be designed such that can be moved back into the loading area by the endless conveyor unit, in particular in the case of a defect. Whenever there is a defect, in particular of the mechanical kind, it is frequently preferable to move the receiving unit involved in the defect out of the defect zone in a direction opposite to the one in which it was conveyed. This facilitates repair of the defect, and operation of the feeding apparatus becomes more reliable.

The endless conveyor unit in particular has a basic position which can preferably be verified by means of an optoelectronic sensor. This referencing allows the stacks to be uniquely numbered and thus clearly allocated. In the case of an electric failure, for example a power outage, the endless conveyor belt will return to its home position and it will thus still be possible to allocate a stack correctly.

It is considered advantageous to have control electronics in place to detect and store the position of the receiving unit in the loading area during loading so that the receiving unit can move back to its original position in the loading area, if necessary, thus remaining allocated to a predetermined holder in the carrier introduced into the loading area. In the event of a defect, any laboratory vessels remaining in the feeding apparatus can then be removed again by means of a carrier and can be introduced in the same configuration into a different feeding apparatus. This increases the degree of automation of the feeding system and saves time.

In an advantageous embodiment of the invention, a sensor, in particular a tactile sensor, is provided in the loading area of the feeding apparatus and is used to detect whether a carrier is present in the loading area. The sensor preferably cooperates with the control electronics in such a way that it will block a conveying action of the endless conveyor unit when a carrier is present in the loading area. This will prevent mechanical damage to the feeding apparatus which prolongs its service life. The sensor can be a microswitch which will not only prevent a conveying action with the carrier in place, but will also only allow opening and closing of the carrier if the latter is in place. Preferably, static mechanical position detection means made of plastic may be provided, i.e. the carrier has a recess and can only be inserted completely if introduced correctly, in which case the microswitch will be actuated, allowing the carrier to be opened and/or closed. The advantage of a "correct" insertion, even if the carrier is of a symmetrical design, in turn is that it will allow the positions of the various stacks to be identified correctly. The stack holders of the carrier are uniquely designated which facilitates allocation. Alternatively, the carrier is of an asymmetrical design.

In one aspect of the invention, a carrier unlocking mechanism is provided in the loading area which will open a carrier that has been introduced correctly in the loading area, if required, so that laboratory vessels can be transferred into a receiving unit, or which will close a carrier so that laboratory vessels contained in a receiving unit can be removed again. In this way, the carrier and the feeding apparatus are more optimally integrated in the feeding system, and in combination with the tactile sensor described above, a higher degree of automation can be achieved.

It is expedient to have sensors in the loading area which will detect whether at least one laboratory vessel is present in the receiving unit, which sensors can preferably take the form of optoelectronic sensors such as light barriers. The optoelectronic sensors allow non-contact measurement. This makes for good electromagnetic compatibility. Empty receiving units can thus be moved on immediately by the endless conveyor unit, and it is ensured that only full receiving units will be accessed in the removal area. This may save a considerable amount of time.

Preferably, the projections for the positive locking of the carrier at the same time also act as a lateral boundary for the laboratory vessels contained in the receiving unit. This simplifies the design and reduces the costs of the feeding apparatus.

In a preferred embodiment, only one receiving unit is allocated to the holder of the carrier. This makes it even easier to allocate a stack of laboratory vessels within the feeding apparatus, and reduces the risk of incorrect referencing.

In an advantageous embodiment of the invention, the carrier has a certain number of holders for the laboratory vessels, and the loading area of the feeding apparatus is constituted by a number of receiving units which corresponds to the number of holders of the carrier. Once the carrier has been inserted, all receiving units in the loading area can be loaded or unloaded. This makes incorrect referencing of the stacks of laboratory vessels virtually impossible once the carrier has been inserted, in particular in combination with the above mentioned positive locking of the carrier and the feeding apparatus. This clearly improves the reliability of the feeding system.

In another aspect of the invention, the endless conveyor unit consists of linear and curved segments. In particular when the unloading area is located in the curved segment of the endless conveyor unit, this geometry alone will prevent loading during an unloading process, thus reducing the danger of a mix-up of stacks and samples.

Preferably, an entire stack of laboratory vessels can be loaded into a receiving unit as a stacked unit from above by means of the carrier, in particular four stacked units at a time into four receiving units. This allows a higher number of laboratory vessels to be introduced into the feeding apparatus in a single loading step, which facilitates operation of the feeding system.

For easier handling of the laboratory vessels, it is advantageous for each stack of laboratory vessels to contain the same type of cultures. This makes it easier to optimally group laboratory vessels for later analysis and the like, and to allocate individual types of cultures.

If every laboratory vessel and every stack are marked so that each laboratory vessel and each stack can be allocated to a position in the loading area and a position in the carrier, this considerably reduces the risk of incorrect allocation. This improves the user friendliness and the reliability of the feeding system. For example, it allows the use of barcodes in combination with appropriate scanners.

Further advantages, features and possible applications of the present invention may be gathered from the description which follows, in which reference is made to the embodiments illustrated in the drawings.

Throughout the description, the claims and the drawings, those terms and associated reference signs are used as are listed in the List of Reference Signs which follows below. In the drawings:

Figure 1:
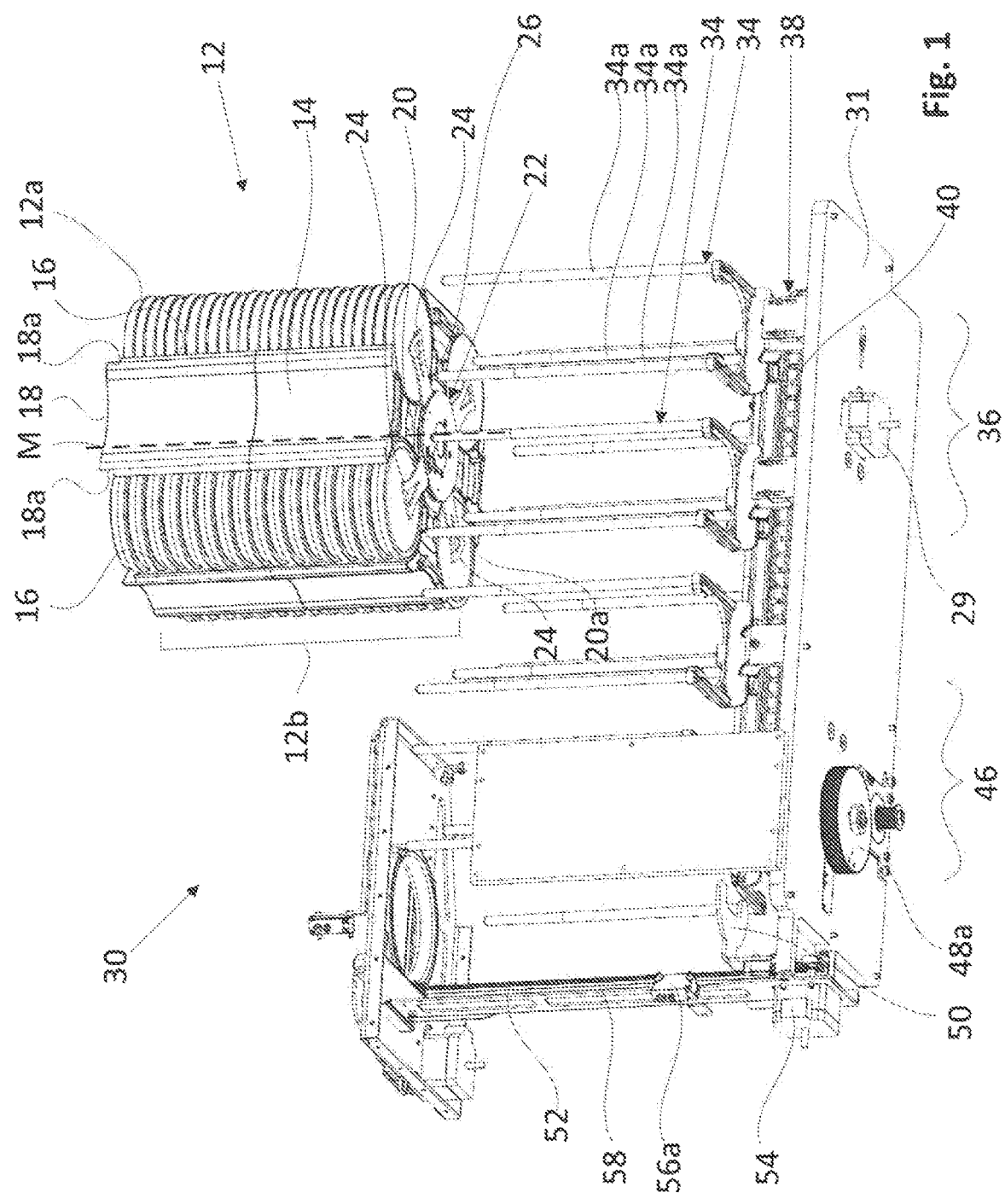
FIG. 1 is a perspective bottom view of the feeding system with a fully loaded carrier in a position before being introduced into the feeding apparatus.
Figure 2:
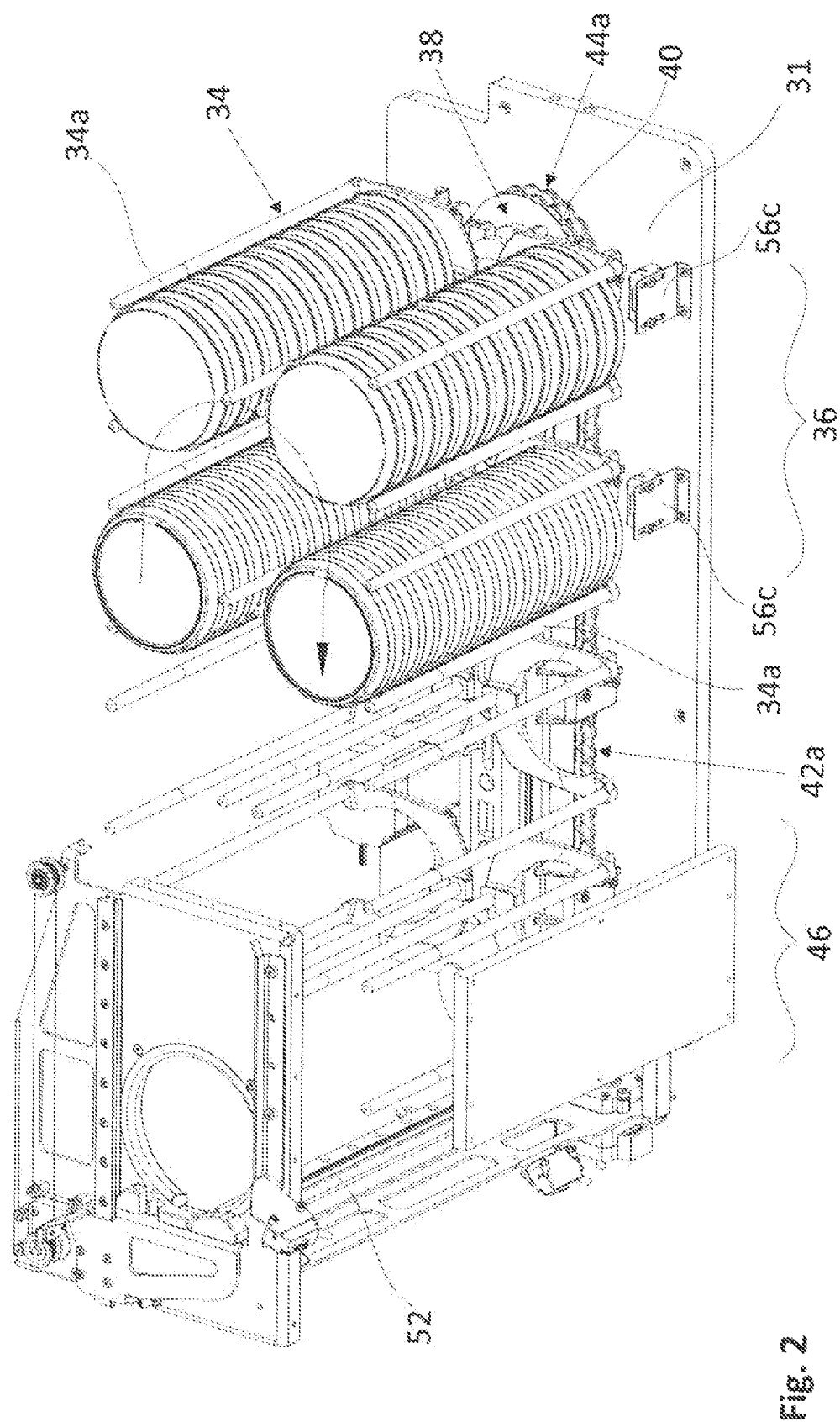
FIG. 2 is a perspective view of the feeding apparatus with four stacks of Petri dishes loaded into a loading area of the feeding apparatus.
Figure 3:
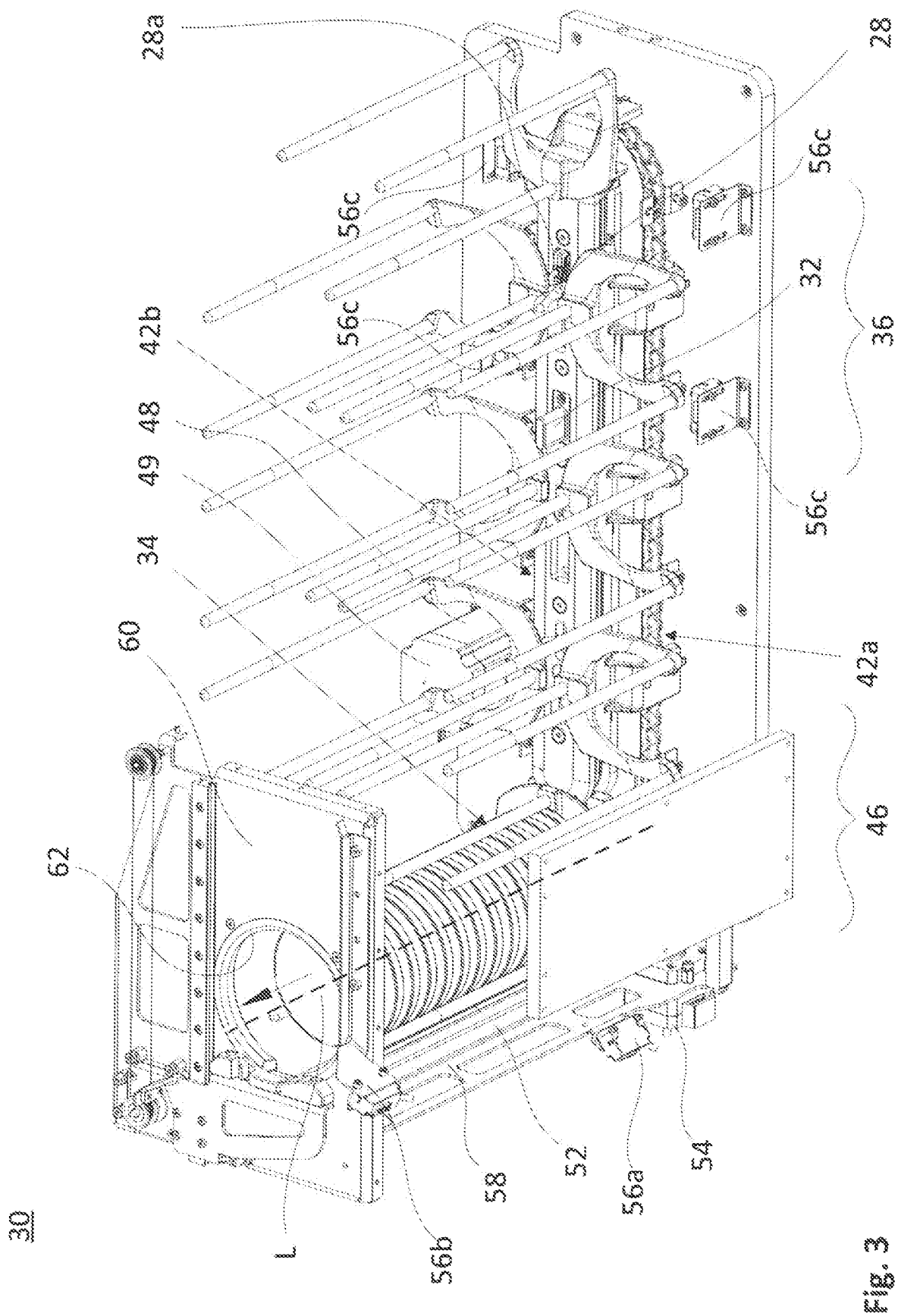
FIG. 3 is a perspective view of the feeding apparatus with one stack of Petri dishes introduced into an unloading area of the feeding apparatus.
Figure 4:
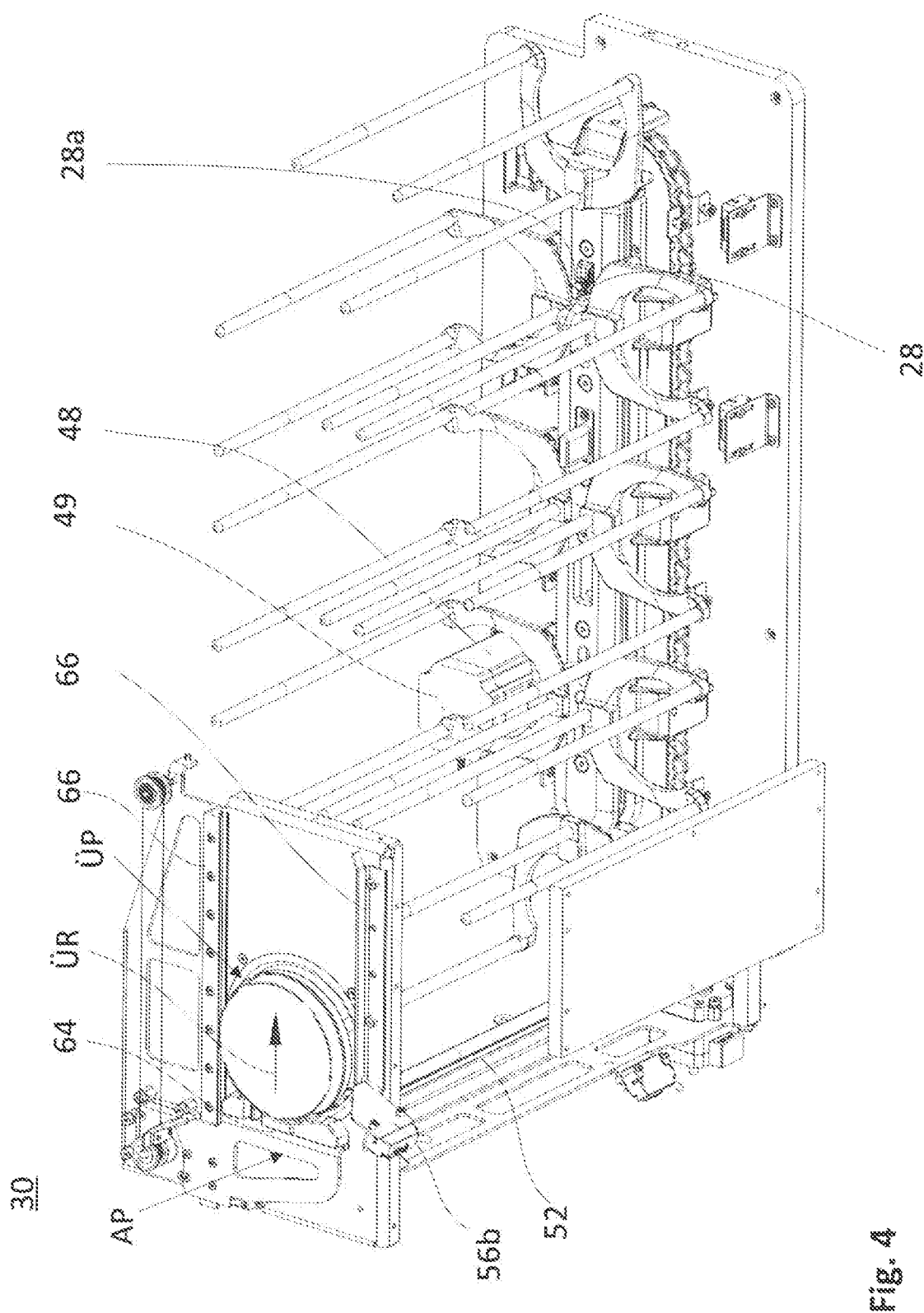
FIG. 4 is a perspective view of the feeding apparatus with a Petri dish held in a transfer area.

FIG. 1 is a perspective bottom view of the feeding system 10 comprising a carrier and a feeding apparatus 30. The carrier 12 is filled with Petri dishes 12a that are vertically arranged on top of each other in a stack 12b and is shown in a position before being inserted in the feeding apparatus 30. FIGS. 2 to 4 are views of the feeding apparatus 30 in different loading states thereof.

A housing 14 of the carrier 12 has four holders 16 arranged in a star-shaped configuration for receiving vertically stacked Petri dishes 12a. The holders 16 are open towards the exterior, but only to such an extent that—while allowing some access from the outside—the Petri dishes 12a can only be removed by vertically sliding them out through an upper loading opening 18a of the holder 16 and no Petri dishes can fall out of the carrier 12. The user can conveniently reach the Petri dishes 12a from the side, but will only be able remove them from above, and the Petri dishes 12a can be safely transported without any danger of them falling out and potentially contaminating the environment. The problem of a Petri dish 12a falling out and cracking open would have serious consequences. It might result in dangerous pathogens being released and contaminating the environment. Moreover, many samples are very precious, e.g. children's bone marrow samples, which need to be handled with the utmost care.

The loading axes of the holders 16 extend in parallel to each other and to a central axis M of the carrier 12. In the housing 14, at the top 18 of the carrier 12, a loading opening 18a is formed each which is used for loading Petri dishes 12a along the loading axis into the respective holder 16. Similarly, at the bottom 20, an unloading opening 20a is formed in the housing 14 through which the Petri dishes 12a are unloaded.

For transport and as a protection from accidental unloading of the Petri dishes 12a, a closing mechanism 22 is provided at the bottom 20 of the carrier 12 which closes the unloading openings 20a of the holders 16. The closing mechanism 22 comprises four sliders 24 which cover the Petri dishes 12a inserted in the holders 16 in a closed state of the closing mechanism 22, thus fixing them along the loading axis in a direction toward the bottom 20.

The sliders 24 are arranged in pairs, and in their closed state, are offset by 90° each relative to each other and arranged concentrically relative to the central axis M of the carrier 12. The two pairs of sliders 24 are coupled to a gear, which is not shown here for the sake of clarity, in particular in the form of a planetary gear, and can be connected to a drive. For a more detailed explanation of the closing mechanism 22, reference is made to German patent application DE 10 2015 207 617.2. In this respect, reference is made to the disclosure of this publication.

At the bottom 20, a recess 26 is furthermore provided in the housing 14 between two holders 16. A pin 28 which is shown in FIG. 3 and which matches the recess 26 is provided in the feeding apparatus 30. When the carrier 12 is properly inserted in the feeding apparatus 30, this pin 28 will engage the recess 26 in a positive locking manner. The carrier 12 can only be inserted fully provided there is a positive fit between the recess 26 and the pin 28.

At the same time, when the pin 28 engages the recess 26, the above mentioned gear is activated, which results in a rotatory movement of the sliders 24 arranged in pairs, causing the closing mechanism 38 to be opened or closed. Activation is carried out by means of a microswitch 28a which is located next to the pin 28, see FIGS. 3 and 4, which sends a signal to a control unit 49 that causes a movement of the pin 28 which allows the carrier 12 to be opened or closed. In this embodiment, closing or opening is initiated by the user via an external user interface. However, this is only possible at all provided that the carrier 12 has been inserted properly. For this purpose, the pin 28 is non-rotatably connected to a drive motor 29 which is arranged beneath the feeding apparatus 30. The control unit 49, which will be explained in more detail below with reference to FIGS. 3 and 4, actuates the drive motor 29 which causes a rotary movement of the pin 28 which in turn activates or deactivates the closing mechanism 22.

When a loaded carrier 12 having its closing mechanism 22 in the closed position is inserted in the feeding apparatus 30, rotary movement of the pin 28 will cause the closing mechanism 22 to be opened. Similarly, for example in the case of a defect, an empty carrier 12 having its closing mechanism 22 in the open position can be inserted into the feeding apparatus 30 loaded with Petri dishes 12a, the closing mechanism 22 can be closed via a rotary movement of the pin 28, and the carrier 12 can be removed together with the Petri dishes 12a.

If the carrier 12 is inserted in an orientation other than the intended one which is defined by the design of the recess 26 and the pin 28 and by position detecting means 32, it will not be possible to fully insert the carrier 12 and opening of the closing mechanism 22 will be prevented.

FIG. 2 is a perspective view of the feeding apparatus 30 with four stacks 12b of Petri dishes 12a introduced into a loading area 36 of the feeding apparatus 30. The stacks 12b of Petri dishes 12a are accommodated in receiving racks 34 which each consist of three vertical rods 34a that extend in parallel to each other and are uniformly spaced from each other relative to the circumference of the Petri dishes 12a.

The receiving racks 34 are mounted on an endless conveyor unit 38 which has a drive (not shown in this Figure) and an endless conveyor chain 40. The conveyor chain 40 runs in a path that has two parallel linear segments 42a, 42b, of which segment 42b can be better viewed in FIG. 3, and two curved segments 44a, 44b. More specifically, segment 44a adjacent to the loading area 36, and curved segment 44b extends adjacent to the unloading area 46 which adjoins the loading area 36, which curved segment 44b is not visible in the perspective chosen for the Figures. The endless conveyor unit 38 is attached to a base plate 31 of the feeding apparatus 30. Moreover, a home switch is provided for finding the home position of the endless conveyor unit 38. For this purpose, a reflector in the form of a small plate is attached to the conveyor chain 40, which reflector cooperates with a forked light barrier. When the reflector passes through the forked light barrier, the endless conveyor unit 38 is in the home position. The reflector and the forked light barrier are arranged accordingly.

A drive motor 48, part of which can be viewed in FIG. 1 beneath the feeding apparatus 30, is provided for driving the endless conveyor unit 38 and is connected to the control unit 49 in a conventional manner. The drive motor 48 is located on the base plate, see FIG. 3, on the bottom side the transmission gear 48a can be viewed which uses gears and a toothed belt. The drive motor 48 can be used to move the conveyor chain 40 together with the receiving racks 34 mounted on it both in a clockwise and a counterclockwise direction. In the loading area 36 of the feeding apparatus 30, the position detection means 32 is mounted on the endless conveyor unit 38. Inserting a carrier 12 in the loading area 36 will activate the microswitch 28a which will send a signal to the control unit 49, which will then block the drive motor 48, thus preventing movement of the endless conveyor unit 38 with the carrier 12 in place. The pin 28 as well as the position detection means will prevent full insertion of the carrier in a direction other than the specified one. The microswitch 28a, see FIG. 3, both prevents movement of the conveyor unit and also only allows loading and/or unloading of the carrier in the active state.

After removal of the carrier 12, with the Petri dishes 12a remaining in the feeding apparatus 30, there will no longer be a signal from the microswitch 28a, and the control unit 49 will release the drive motor 48. Moreover, photoelectric sensors 56c are provided on the base plate 31 in the loading area 36 and are connected to the control unit 49, which sensors 56c will detect whether there is at least one Petri dish 12a each in the receiving racks 34 present in the loading area 36.

Receiving racks 34 filled with stacks 12b of Petri dishes 12a will be conveyed from the loading area 36 to the unloading area 46 in a clockwise direction so that another four empty receiving racks 34 for receiving stacks 12b of Petri dishes 12a from another carrier 12 will be available. The feeding apparatus 30 can thus be loaded with up to eight stacks 12b of Petri dishes 12a at a time. The endless conveyor unit 38 which can be moved both in a clockwise and a counterclockwise direction thus ensures that the stacks 12b of Petri dishes 12a can be processed in the desired order. Moreover, in the case of a defect, it will be possible, depending on the current conveying position, to return the receiving racks 34 faster counterclockwise to the position they had when the carrier 12 was inserted, and to remove the stacks 12b of Petri dishes 12a again in their original orientation relative to each other.

For the sake of clarity, only one stack 12b of Petri dishes 12a introduced into the unloading area 46 of the feeding apparatus 30 is shown in FIG. 3. A transfer plate 60 which is spaced from the base plate 31 via a linear connecting rail 58 is mounted above the unloading area 46, in parallel to the base plate 31 of the feeding apparatus 30. The transfer plate 60 serves to transfer Petri dishes 12*a* to another system connected to the feeding apparatus 30, for example an analysis unit, as described below.

For transporting the Petri dishes 12*a* from the stack 12*b* of Petri dishes 12*a* to the transfer plate 60, a receiving rack 34 loaded with a stack 12*b* of Petri dishes 12*a* is moved to the curved segment 44*b* of the endless conveyor unit 38. At the end associated with the unloading area 46 of the feeding apparatus 30, an elevator fork 50 is provided which in the standby condition is arranged beneath the curved segment 44*b* of the endless conveyor unit 38. The elevator fork 50 can be best seen in the view of FIG. 1. The elevator fork 50 can be moved vertically along an elevator axis L via an elevator rail 52 mounted on the linear connecting rail 58. The elevator is driven by a conventional electric motor 54 connected to the control unit 49 which is arranged on the side of the elevator rail 52 facing away from the elevator fork 50 and drives the movement of the elevator fork via a toothed belt.

A photoelectric sensor 56*a* provided on the connecting rail 58 is likewise connected to the control unit 49. As soon as the photoelectric sensor 56*a* and the fork light barrier integrated in the base plate 31 detect the presence of a receiving rack 34 loaded with at least one Petri dish 12*a* in the curved segment 44*b* of the endless conveyor unit 38 and a corresponding signal is transmitted to the control unit 49, the control unit 49 will control the electric motor 54 to cause it to move the elevator fork 50. The elevator fork 50 then travels along the elevator rail 52 to underneath the stack 12*b* of Petri dishes 12*a* and continues with the stack 12*b* of Petri dishes 12*a* in the direction of the transfer plate 60.

The transfer plate 60 has an essentially circular hole 62 whose diameter at 9.4 cm is large enough for Petri dishes 12*a* of all common sizes to pass through it. The elevator fork 50 travels toward the transfer plate 60 to such an extent that the topmost Petri dish 12*a* passes through the hole 62 and enters a transfer position TP as illustrated in FIG. 4.

In the transfer position TP, the topmost Petri dish 12*a* has completely passed through from the hole 62 at the top of the transfer plate 60 and can thus be moved horizontally on the transfer plate 60. Once the transfer position TP has been reached, this is detected by a photoelectric sensor 56*b* mounted on the transfer plate 60 which signals it to the control unit 49 that then controls the electric motor 54 so as to stop the vertical movement of the elevator fork 50.

FIG. 4 is a view of the feeding apparatus 30 having a Petri dish 12*a* in the transfer position TP. A pusher 64 is mounted on the transfer plate 60 which can be moved along the transfer plate 60 via two rails 66 that extend in parallel. In a starting position SP illustrated in FIGS. 1 to 4, the pusher 64 is above the elevator fork 52, in which it does not cover the area above the hole 62, so that a Petri dish 12*a* can be moved into the transfer position TP in the above described manner. The pusher 64 will push the Petri dish 12*a* resting on the elevator fork 50 in the transfer position TP into a transfer direction TD on the transfer plate 60.

In a state of the feeding apparatus 10 in which it is connected to another system, for example an analysis unit, a conveyor means is arranged at the end of the transfer plate 60 which is remote from the hole 62, which conveyor means takes over the Petri dishes 12*a* and transports them to a camera chamber, for example.

As soon as the pusher 64 has moved the Petri dish 12*a* out of the transfer position TP and the pusher 64 has resumed its starting position SP, the elevator fork 50 continues further along the linear elevator rail 52 in the direction of the transfer plate 60 until the next Petri dish 12*a* reaches the transfer position TP.

After the bottommost Petri dish 12*a* of a stack 12*b* has been moved onto the transfer plate 60, the elevator fork 50 moves into the above mentioned position underneath the curved segment 44*b* of the endless conveyor unit 38. Another receiving rack 34 loaded with a stack 12*b* of Petri dishes 12*a* is moved to the curved segment 44*b* of the endless conveyor unit 38. Then the Petri dishes 12*a* of the next stack 12*b* of Petri dishes 12*a* can be transported to the system connected to the feeding apparatus 30.

Figure 5:
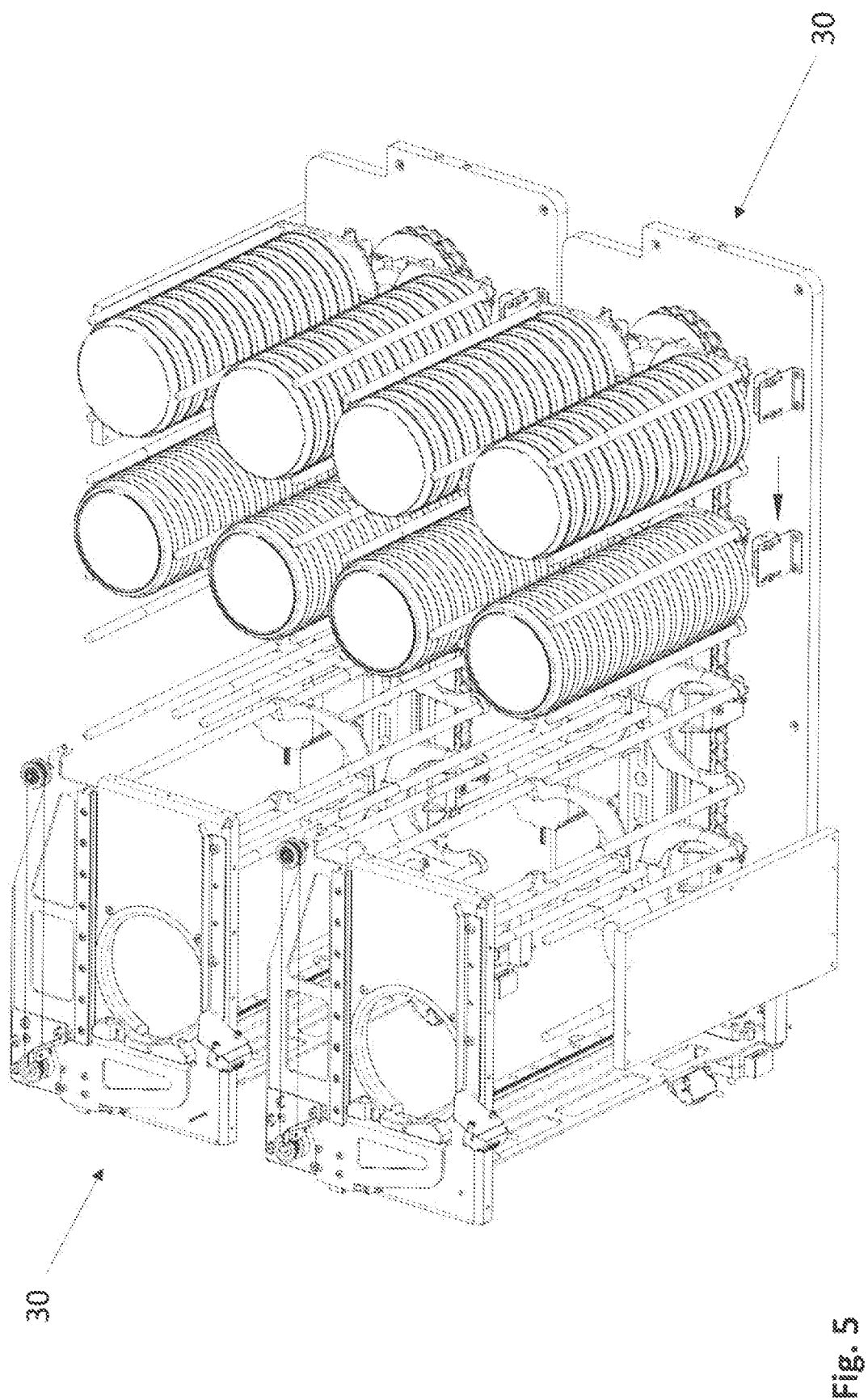
FIG. 5 is an embodiment of the invention with two feeding apparatuses aligned in parallel to one another.

FIG. 5 is a view of an embodiment of the invention which has two feeding apparatuses 30 arranged in parallel. Providing plural feeding apparatuses 30 next to each other will allow the receiving capacity of the feeding system 10 to be increased several times over.

LIST OF REFERENCE SIGNS

10 feeding system
12 carrier
12*a* Petri dish
12*b* stacks of Petri dishes 12*a*
14 housing
16 holder
18 top
18*a* loading opening
20 bottom
20*a* unloading opening
22 closing mechanism
24 slider
26 recess
28 pin
28*a* microswitch
29 drive motor
30 feeding apparatus
31 base plate
32 position detection means
34 receiving rack
36 loading area
38 endless conveyor unit
40 conveyor chain
42*a, b* linear segments
44*a, b* curved segments
46 unloading area
47 gearwheel
48 drive motor
48*a* transmission gear
49 control unit
50 elevator fork
52 elevator rail
54 electric motor
56*a, b, c* photoelectric sensors
58 connecting rail
60 transfer plate
62 hole
64 pusher
66 rails
L elevator axis
M central axis
SP starting position
TP transfer position
TD transfer direction

The invention claimed is:

1. Feeding system (10), comprising:
a feeding apparatus (30) for conveying laboratory vessels for samples, microorganisms, and cell cultures;
a movable carrier (12) includes a plurality of holders (16) for storing a plurality of laboratory vessels;
said feeding apparatus (30) has a loading area (36) and an unloading area (46) remote from said loading area (36);
said plurality of laboratory vessels are arranged in a vertically stacked configuration in said holders of said feeding apparatus (30);
said feeding apparatus includes a plurality of receiving units (34) and an endless conveyor unit (38);
each of said receiving units (34) is coupled to said endless conveyor unit (38);
said endless conveyor unit transports said receiving units (34) from said loading area (36) to said unloading area (46);
said carrier (12) introduces said plurality of holders of said plurality of laboratory vessels into said plurality of receiving units (34) in said loading area (36) of said feeding apparatus;
said carrier (12) and said plurality of holders of said plurality of laboratory vessels are removably slid over said receiving units (34) which is/are to be loaded or unloaded;
said feeding apparatus (30) includes at least one projection (28) in said loading area (36);
said carrier includes at least one recess;
said at least one projection (28) of said feeding apparatus positively locks and engages said feeding apparatus (30) and said recess of said carrier (12) when said carrier (12) is inserted in said loading area (36);
said holders include a bottom portion;
a closing mechanism (22) at said bottom portion of said holders (16) supporting said vessels;
said closing mechanism includes sliders, said sliders support said vessels in said holders (16);
said sliders being rotatable when said projection (28) engages said recess;
said positive locking of said carrier (12) and said receiving unit (34) of said feeding apparatus (30) in said loading area (36) of said feeding apparatus (30) allows only a single predefined orientation of said carrier (12) in said loading area (36).

2. Feeding system according to claim 1, further comprising:
each of said receiving units (34) are returnable to said loading area (36) by said endless conveyor unit (38).

3. Feeding system according to claim 1, further comprising:
each of said receiving units (34) allow stacks (12b) of laboratory vessels (12a) to be inserted only in a defined orientation.

4. Feeding system according to claim 3, further comprising:
a mechanical barrier (28, 33) prevents said carrier unit (12) from being oriented improperly.

5. Feeding system according to claim 1, further comprising:
a control unit (49) detects and stores the position of said receiving unit (34) in said loading area (36) during loading so that, if necessary, said receiving unit (34) is returned to an original position in said loading area (36) and thus remains associated with a predetermined holder (16) in said carrier (12) introduced into said loading area (36).

6. Feeding system according to claim 1, further comprising:
a sensor (28a) in said loading area (36) of said feeding apparatus (30) detects whether said carrier (12) is present in said loading area (36);
said sensor (28a) cooperates with said control unit (49) so as to prevent a conveying action of said endless conveyor unit (38) when said carrier (12) is present in said loading area (36).

7. Feeding system according to claim 1, further comprising:
an unlocking mechanism (28, 26) for said carrier (12) in said loading area (36);
said unlocking mechanism will open said carrier (12) introduced into said loading area (36) if necessary, so that laboratory vessels can be transferred into at least one of said receiving units (34), or said unlocking mechanism will close said carrier so that any laboratory vessels present in at least one of said receiving units (34) can be removed again.

8. Feeding system according to claim 1, further comprising:
sensors (54a, 54c) in said loading area (36) detect whether at least one laboratory vessel is present in at least one of said receiving units (34);
said sensors (54a, 54c) are light barriers.

9. Feeding system according to claim 1, further comprising:
protrusions for positive locking of the carrier (12) at the same time also constitute a lateral boundary for the laboratory vessels introduced into at least one of said receiving units (34).

10. Feeding system according to claim 1, further comprising:
a single receiving unit (34) only is allocated to a holder of said carrier (12).

11. Feeding system according to claim 8, further comprising:
the number of said plurality of said receiving units (34) corresponds to the number of holders (16) of said carrier (12) so that, with said carrier (12) in place, all of said receiving units (34) in said loading area (36) can be loaded or unloaded.

12. Feeding system according to claim 1, further comprising:
said endless conveyor unit (38) runs in a path which has linear segments (42a, 42b) and curved segments (44a, 44b).

13. Feeding system according to claim 1, further comprising:
at least one entire stack of laboratory vessels can be introduced as a stacked unit from above into said receiving unit (34) by said carrier (12).

14. Feeding system according to claim 13, further comprising:
four stacked units at a time are introduced into four receiving units (34).

15. Feeding system according to claim 1, further comprising:
each laboratory vessel and each stack is marked such that each said laboratory vessel and each said stack can be allocated to a position in said loading area (36) and to a position in said carrier (12).

* * * * *